//

US006774213B1

(12) United States Patent
Roca

(10) Patent No.: US 6,774,213 B1
(45) Date of Patent: Aug. 10, 2004

(54) MUTANTS OF MAW MOTIFS OF RECA PROTEIN HOMOLOGS, METHODS OF MAKING THEM, AND THEIR USES

(75) Inventor: Alberto I. Roca, 13702 Teal Shore Ct., Houston, TX (US) 77077-3421

(73) Assignee: Alberto I. Roca, Houston, TX (US)

( * ) Notice: Subject to any disclaimer, the term of this patent is extended or adjusted under 35 U.S.C. 154(b) by 0 days.

(21) Appl. No.: 09/358,103

(22) Filed: Jul. 21, 1999

Related U.S. Application Data

(60) Provisional application No. 60/094,071, filed on Jul. 24, 1998.

(51) Int. Cl.[7] ................................................. C07K 1/00
(52) U.S. Cl. ........................ 530/350; 435/183; 435/193; 435/252.8; 530/350; 536/23.1; 536/23.2
(58) Field of Search ................................. 435/183, 193, 435/252.8, 195, 252.33; 530/350; 536/23.1, 23.2

(56) References Cited

U.S. PATENT DOCUMENTS

| | | | | |
|---|---|---|---|---|
| 5,643,758 A | * | 7/1997 | Guan et al. ................. | 435/69.7 |
| 6,008,031 A | | 12/1999 | Modrich et al. | |
| 6,242,211 B1 | | 6/2001 | Peterson et al. | |

OTHER PUBLICATIONS

Menetski et al. Interaction of recA protein with single-stranded DNA. Quantitative aspects of binding affinity modulation by nucleotide cofactors. J Mol Biol. Jan. 20, 1985, vol. 181, pp. 281–95.*
Konola et al. Mutations at Pro67 in the RecA protein P–loop motif differentially modify coprotease function and separate coprotease from recombination activities. J Biol Chem. Apr. 14, 1995, vol. 270, pp. 8411–8419.*
Story et al. Structure of the recA protein–ADP complex. Nature. Jan. 23, 1992, vol. 355, pp. 374–6.*
Story et al. Structural relationship of bacterial RecA proteins to recombination protesin from bacteriophage T4 and yeast. Science. Mar. 26, 1993, vol. 259, pp. 1892–6.*
S. Sommer, F. Boudsocq, R. Devoret & A. Bailone, Specific RecA Amino Acid Changes Affect RecA–UmuD'C Interaction, Molecular Microbiology 28:281 (1998).

P. Howard–Flanders & L. Theriot, Mutants of Escherichia coli K–12 Defective in DNA Repair and in Genetic Recombination, Genetics 53:1137 (1966).
A.J. Clark, The Beginning of a Genetic Analysis of Recombination Proficiency, Journal of Cellular Physiology 70:165 (1967).
S.D. Lauder & S.C. Kowalczykowski, Negative Co–dominant Inhibition of RecA Protein Function: Biochemical Properties of the RecA1, RecA13, and RecA56 Proteins and the Effect of RecA56 Protein on the Activities of the Wild–type RecA Protein Function In Vitro, Journal of Molecular Biology 234:72 (1993).
B.P. Rubin, D.O. Ferguson & W.K. Holloman, Structure of REC2, a Recombinational Repair Gene of Ustilago maydis, and Its Runction in Homologous Repair Between Plasmid and Chromosonal Sequences, Molecular and Cellular Biology 14:6287 (1994).
P.E. Lavery & S.C. Kowalczykowski, Biochemical Basis of the Constitutive Repressor Cleavage Activity of RecA730 Protein: A Comparison to RecA441 and RecA803 Proteins, Journal of Biological Chemistry 267:20648 (1992).
M.V.V.S. Madiraju, P.E. Lavery, S.C. Kowalczykowski & A.J. Clark, Enzymatic Properties of the RecA803 Protein: A Partial Suppressor of recF Mutations, Biochemistry 31:10529 (1992).
M.J. Campbell & R.W. Davis, On the In Vivo Function of the RecA ATPase, Journal of Molecular Biology, 286:437 (1999).

* cited by examiner

Primary Examiner—Nashaat T. Nashed
Assistant Examiner—Christian L Fronda
(74) Attorney, Agent, or Firm—Connolly Bove Lodge & Hutz LLP; Christopher E. Jeffers

(57) ABSTRACT

RecA protein mutants and RecA homolog protein mutants which contain one or more mutations in the MAW motif are presented. The mutants rely on replacement of wildtype amino acid residues in the MAW motif with specific replacement residues to alter the three-dimensional structure of the MAW motif and to change the protein's DNA-binding properties. Three classes of mutants are described: mutants which will reduce the protein's dependence on ATP to initiate DNA-binding; mutants which more tightly bind DNA; and combination mutants which possess both of these properties.

27 Claims, 3 Drawing Sheets

| position | 40 | | | 45 | | | | 50 | | | | 55 | | | 60 | | | | 65 | | |
|---|---|---|---|---|---|---|---|---|---|---|---|---|---|---|---|---|---|---|---|---|---|
| MAW motif | i | x | t | g | x | x | x | l | d | x | a | l | x | x | G | G | l | x | x | g | x | i | v | E | i | y |

α Helix B          β Strand 1

```
E. coli RecA      I S T G S L S L D I A L G A G G L P M G R I V E I Y
bacterial RecA    F G S R A I A I N A   M   I     F   G   V I   V F
                  M K       C T D V     E   T     S   I K     T
                  T P       I V G       G         T   V R
                  V         N Y L       L         V   Y
                  Y             M       N         Δ
                                T       Q
                                V       R
                                Y       S
                                        T
                                        V Rad51 & Dmc1      I S T G S K A L D E I L G Δ G G I E T G Q I T E A F
                  L T       Q   E     K L Q       V M   L S       L
                            N         S               M         M
                            Q         T                           V RecA/Rad51-like   F R S A D D A F D D A L A G G G F E A A G A I E F A
                  I S T G F K E L N E I     G L   I F K G R I T I I F
                  L T W K I L G M   G L   N Δ     L P P H S L V L L G
                  V       N S P M V I V   S ^     M Q S Q T M Y   V V
                          Q   Q N     L           V R T R V V       Y
                              R T     R             V     ^
                              T       T
                              V MAW mutants                         W     W         W       W
                                    Y                       Y
```

Fig. 1

MUTANTS OF MAW MOTIFS OF RECA PROTEIN HOMOLOGS, METHODS OF MAKING THEM, AND THEIR USES

CROSS REFERENCE TO RELATED APPLICATIONS

This application claims the benefit of U.S. Provisional Application No. 60/094,071, filed Jul. 24, 1998.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. GM 32355 awarded by NIH.

BACKGROUND OF THE INVENTION

(1) Field of the Invention

The invention concerns the invention and production of mutant RecA homolog proteins by substituting amino acid residues at particular residue positions along the MAW (Makes ATP Work) motif. The MAW motif is defined as amino acid residues 40 to 65 in the *Escherichia coli* (*E. coli*) RecA protein (SEQ ID NO: 1) and the homologs of this structure in other proteins. These mutants are classified as Class V, VI, and VII mutants. Class V mutants of this form can be active independently of ATP, which is required to activate wildtype RecA. Class VI mutants of this form can exhibit tighter binding to DNA than wildtype RecA. Class VII mutants exhibit combinations of Class V and VI mutant properties to provide both ATP-independence and tighter DNA binding.

(2) Description of the Related Art

The RecA protein of *E. coli* is an important player in the in vivo processes of homologous recombination and recombinational DNA repair. Its functions in vivo depend upon several key activities identified in vitro, including the binding of multiple DNA molecules and the hydrolysis of ATP. Such ligand interactions allow the detection of complementary sequences between homologous DNA molecules, generating a Holliday-like structure after strands are exchanged. The RecA protein also promotes branch point migration to resolve this intermediate structure.

Nature also highlights the significant role of the RecA protein by using it as the regulator of the SOS response. (Friedberg, et al., in *DNA Repair and Mutagenesis*, ASM Press, Washington, D.C. 1995, p. 407) The existence of damaged DNA signals the RecA protein to become activated. This switch promotes the autoproteolysis of the LexA repressor upon binding to a RecA-DNA-ATP complex. Once the LexA repressor is inactivated, a number of protein products are produced, including the RecA protein. Many of these SOS proteins act at the site of DNA damage after the RecA protein has initiated the repair process through recombinational DNA repair. Thus, the RecA protein is an important genomic sentinel for *E. coli* since it identifies problems and organizes their correction—all of which ensures the integrity of an organism's genetic information.

One relatively unexplored region of the RecA protein is the recently defined MAW (Makes ATP Work) motif, located at residues 40–65. It has been proposed that this is part of the conformational switch of the RecA protein that signals the ADP- vs ATP-bound state. It is well established that the RecA protein exhibits different conformations in response to cofactors. (Egelman & Stasiak, Micron 24:309 (1993)).

There are some known mutations of RecA and homologous proteins, within the MAW motif and elsewhere, which relate to either ATP interaction or DNA binding, S. Sommer, F. Boudsocq, R. Devoret, and A. Bailone, Specific RecA Amino Acid Changes Affect RecA-UmuD'C Interaction, Molecular Microbiology 28:281 (1998) discloses a mutation within the MAW motif, substituting leucine for serine at position 44 (44SL) (Mutants are herein denoted by the position number, the letter designation of the removed residue, and the letter designation of the substituted residue; thus, "44SL" denotes a serine to leucine switch at position 44). This mutation was isolated randomly through a genetic screen. The in vivo phenotype shows that the mutant behaves like wildtype RecA protein except when it interacts with *E. coli* protein UmuD'C. Biochemical information regarding the characteristics of 44SL is not available.

P. Howard-Flanders and L. Theriot, Mutants of *Escherichia coli* K-12 Defective in DNA Repair and in Genetic Recombination, Genetics 53:1137 (1966) discloses a substitution of leucine to phenylalanine at position 51(51LF) within the MAW motif in RecA13. This mutation was shown to be inactive in vivo. Further, S. D. Lauder and S. C. Kowalczykowski, Negative Co-dominant Inhibition of RecA Protein Function: Biochemical Properties of the RecA1, RecA13, and RecA56 Proteins and the Effect of RecA56 Protein on the Activities of the Wild-type RecA Protein Function In Vitro, Journal of Molecular Biology 234:72 (1993) demonstrated that this mutant is inactive in vitro. As discussed below, the substitution occurs at a special location in the MAW structure, and the phenylalanine is insufficiently large to affect the activity of the protein in this position.

In A. J. Clark, The Beginning of a Genetic Analysis of Recombination Proficiency, Journal of Cellular Physiology 70:165 (1967), a RecA56 mutant within the MAW motif is disclosed. This mutant substitutes cysteine for arginine at position 60 (60RC). This mutant was shown in the original disclosure to be inactive in vivo. It has also been shown to be inactive in vitro. See S. D. Lauder and S. C. Kowalczykowski, Negative Co-dominant Inhibition of RecA Protein Function: Biochemical Properties of the RecA1, RecA13, and RecA56 Proteins and the Effect of RecA56 Protein on the Activities of the Wild-type RecA Protein Function In Vitro, Journal of Molecular Biology 234:72 (1993). This substitution is from a volumetrically larger to a smaller residue.

Other mutants in the MAW motif have been disclosed in *Ustilago maydis fungi*. See B. P. Rubin, D. O. Ferguson, and W. K. Holloman, Structure of REC2, a Recombinational Repair Gene of *Ustilago maydis*, and Its Function In Homologous Recombination Between Plasmid and Chromosonal Sequences, Molecular and Cellular Biology 14:6287 (1994). This work disclosed five mutants within the MAW motif: rec2-4, substituting alanine for serine at position 42 (42SA); rec2-5, substituting alanine for aspartate at position 48 (48DA); rec2-2, substituting phenylalanine for leucine at position 51 (51LF); rec2-6, substituting alanine for glycine at position 54 (54GA); and rec2-7, substituting alanine for glycine at position 55 (55GA). The 42SA and 55GA mutants involve volumetrically small (alanine) substitutions and behave like the wildtype protein. The 48DA, 51LF, and 54GA mutants are defective in UV damage repair as compared to the wildtype protein. 48DA and 54GA involve volumetrically small substitutions. Although 51LF involves a larger (phenylalanine) substitution, it is located at a geometrically special position in the three-dimensional structure of the MAW motif, and is insufficiently large to enhance the DNA binding properties of the protein.

Other *E coli* protein mutants are known which bind DNA better than the wildtype protein. See P. E. Lavery and S. C. Kowalczykowski, Biochemical Basis of the Constitutive Repressor Cleavage Activity of RecA730 Protein: A Comparison to RecA441 and RecA803 Proteins, Journal of Biological Chemistry 267:20648 (1992), and M. V. V. S. Madiraju, P. E. Lavery, S. C. Kowalczykowski, and A. J. Clark, Enzymatic Properties of the RecA803 Protein: A Partial Suppressor of recF Mutations, Biochemistry 31:10529 (1992). These publications disclose substitution of methionine for valine at position 37 (37VM) in RecA803, substitution of lysine for glutamate at position 32 (32EK) in RecA441, and substitution of valine for isoleucine at position 298 (298IV) in RecA441. These publicly available RecA803 and RecA441 mutants bind DNA more quickly than wildtype RecA. However, these mutants still require an ATP-like cofactor.

Similarly, the substitution of aspartate for glutamate at position 96 (96ED) in RecA is disclosed in M. J. Campbell and R. W. Davis, On the In Vivo Function of the RecA ATPase, Journal of Molecular Biol. 286:437 (1999). 96ED allows the mutant RecA protein to bind ATP and prevent its hydrolysis, thus keeping the mutant RecA active. However, this mutant is not free of the requirement for the ATP cofactor.

It is desirable to produce a cofactor-independent RecA protein. It is also desirable to produce a RecA protein which binds DNA better than wildtype RecA. The above listed mutants do not meet these goals because they are either inactive, or because they still require a cofactor to activate.

BRIEF SUMMARY OF THE INVENTION

The invention presents RecA homolog protein mutants which have mutations within the MAW motif. The MAW motif is highly conserved among various species, as shown in the sequence analysis of A. I. Roca & M. M. Cox, Progress in Nucleic Acid Research and Molecular Biology 56:129–223 (1997). The MAW motif is defined as amino acid residues 40 to 65 in the *Escherichia coli* (*E. coli*) RecA protein (SEQ ID NO: 1) and the homologs of this structure in other proteins. Therefore, as used throughout, the term "RecA homolog protein" refers to an *E. coli* RecA protein having the MAW sequence at residues 40–65, inclusive, as shown in SEQ ID NO: 1, or a homolog thereof. These homologs include, but are not limited to, homologs in bacteria, viruses, archaea, and eukaryotes (in particular, human). Examples of these RecA homolog proteins are: bacteria (e.g., *E. coli*) RecA proteins; viruses (e.g., bacteriophage T4) UvsX proteins; Archaea (e.g., *Methanococcus jannaschih*) RadA proteins; and Eucarya (e.g., *Homo sapiens*) Rad51, Dmc1, and Lim15 proteins. In each of these RecA homolog proteins, the MAW motif is identified as the structural homolog of the *E. coli* RecA MAW motif. (See SEQ ID NO: 1; Roca & Cox, supra).

The mutations of this invention modify the MAW region's properties as an ATP-induced conformational switch and as a DNA binding site of the RecA protein. These mutations involve selectively replacing one or more naturally occurring amino acid residues within the MAW motif with volumetrically larger residues (Class V mutants), or by replacing one or more naturally occurring residues with aromatic residues (Class VI mutants). Class V mutants are mutants which will be active independently of cofactors such as ATP or ATPγS. To achieve this goal, the replacement residue must be sufficiently large, that is, as large or larger than phenylalanine.

Thus, the term "RecA homolog protein mutant" as used herein refers to an *E. coli* RecA protein, or a bacterial, eukaryotic, archaeal, or viral homolog thereof, in which the naturally occurring MAW motif has been modified by one or more such replacements of amino acid residues. "Volumetrically larger," as used herein in reference to a replacement residue, means a residue which is larger than the residue it replaces, and which is as large or larger than phenylalanine.

Because the MAW motif is three-dimensional, the selective positioning of an amino acid residue replacement will affect the physical structure of the MAW motif in a RecA homolog protein mutant. Thus, selective position of such replacements will also affect the behavior of a RecA homolog protein mutant, and this positioning can be controlled to produce particular results. As referred to herein, "Class V mutants" are those mutants which will generally reduce the dependence of the RecA homolog protein mutant on the presence of ATP to initiate DNA binding. Examples of Class V mutants are those with replacements at residues 43, 52, 53, 54, 55, or 59, or combinations thereof. Similarly, "Class VI mutants" are those mutants which will generally bind DNA more tightly than the wildtype RecA homolog proteins from which they are derived. Examples of Class VI mutants are those with aromatic replacements at residues 40, 42, 44, 47, 50, 51, or 56, or combinations thereof. However, the three-dimensional structure of the MAW motif is such that positions 47 and 51 are "special" sites, requiring a sufficiently volumetrically large aromatic substitution, that is, tryptophan, to meet this goal. Combinations of Class V and Class VI mutations are referred to herein as "Class VII mutants," and will generally exhibit the advantages of Class V and Class VI mutants.

In creating Class V mutants, replacement amino acid residues are selectively volumetrically larger than the wildtype residues which they replace to force structural alterations within the three-dimensional MAW motif, and sufficiently volumetrically large to place the protein in an "open and active" state. Therefore, those skilled in the art will recognize that preferable replacement amino acid residues in Class V mutants will be selected from the group of phenylalanine, lysine, tyrosine, arginine, and tryptophan. In creating Class VI mutants, naturally occurring residues are replaced with aromatic residues. Accordingly, those of skill in the art will recognize that preferable replacement amino acid residues in Class VI mutants will be selected from the group of tryptophan, tyrosine, phenylalanine, and histidine. Because of the special nature of positions 47 and 51, it will be recognized that, for these positions, tryptophan is the only aromatic replacement which will be sufficiently large to enhance DNA binding. For example, substitution of tyrptophan for leucine at position 47 (47LW) is active whereas substitution of tyrosine in this position (47LY) is not. This situation is in contrast to that at position 56, where substitution by either tyrosine (56LY) or tryptophan (56LW) is active. (See FIG. 2). In both Class V and VI mutants, tryptophan is the most preferred replacement amino acid residue.

It is an object of this invention to provide RecA homolog protein mutants which are ATP-independent and which can replace RecA in applications which currently require ATP.

It is a further object of this invention to provide RecA homolog protein mutants which provide tighter DNA binding compared to wildtype RecA.

BRIEF DESCRIPTION OF THE FIGURES

FIG. 1 is a schematic representation of the MAW motif and its distribution in the bacterial, viral, archaeal, and eukaryotic RecA homologs, together with a schematic representation of certain RecA mutants.

DETAILED DESCRIPTION OF THE INVENTION

1) Overview

Figure 2:
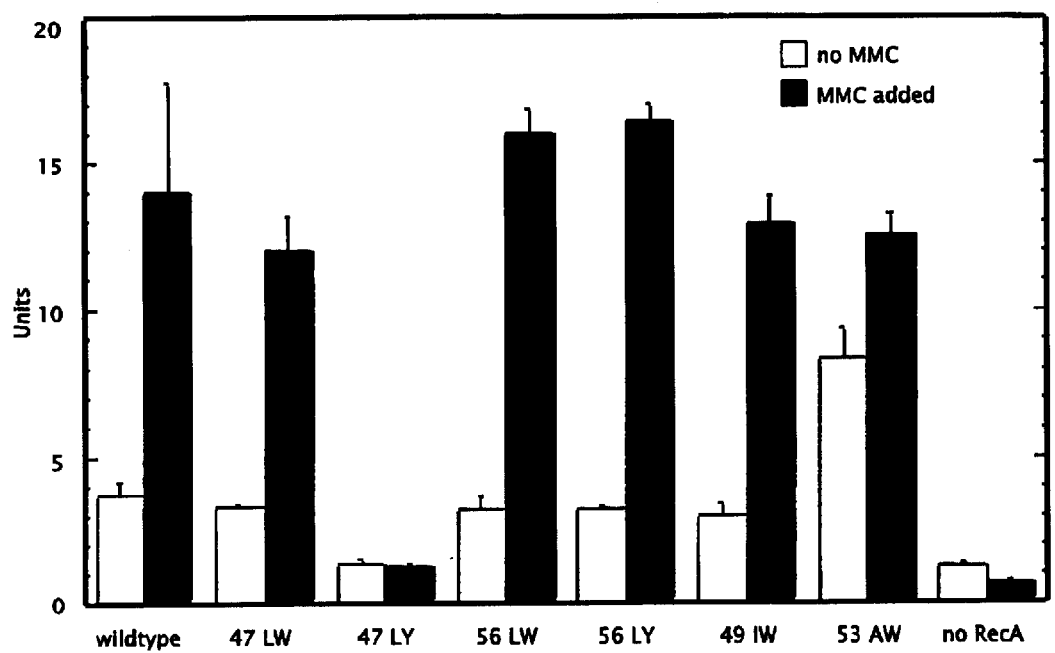
FIG. 2 is a graph showing LexA cleavage assay results for examples of MAW mutants and providing comparisons with wildtype RecA results and results in the absence of RecA.

The invention presents RecA homolog protein mutants which have mutations within the MAW motif. These mutants may be produced in RecA homolog proteins, including those of organisms whose MAW sequences are compared in FIG. 1. The MAW motif is found in all the listed RecA proteins and their homologs.

As an illustration, FIG. 1 schematically presents the sequence of the MAW motif and its distribution in the bacterial, viral, archaeal, and eukaryotic RecA homologs. The data was obtained by applying the sequence alignment method described in A. I. Roca & M. M. Cox, Progress in Nucleic Acid Research and Molecular Biology 56:129–223 (1997) and the data was used to produce FIG. 1. In the line labeled "MAW motif", uppercase letters represent invariant residues. (See SEQ ID NO: 2). Lowercase letters represent semiconservative changes. (See SEQ ID NO: 3). A triangle (Δ) represents a one-residue deletion. "^" indicates an insertion of one or more amino acid residues. The positions of the secondary structural elements are indicated by thick horizontal lines and are labeled "α helix B" and "β strand 1" as determined by R. M. Story, I. T. Weber & T. A. Steitz, Nature 355:318–325 (1992).

The RecA homolog proteins used for the FIG. 1 analysis are the sixty-four bacterial RecA homologs and the 9 eukaryotes, 1 bacteriophage, and 1 archaea described in FIGS. 4 and 9 of A. I. Roca & M. M. Cox, Progress in Nucleic Acid Research and Molecular Biology 56:129–223 (1997) and the 2 archaeal homologs (Haloferax volcanii and M Jannaschii) described in S. J. Sandler, L. H. Satin, H. S. Samra, & A. J. Clark, Nucl. Acids Res. 24:2125–2133 (1996). Examples of the RecA homolog proteins analyzed in FIG. 1 are those from: humans, mice, *E. coli*, *Saccharomyces cerevisiae*, *Thermus aquaticus*, and *Bacillus subtilis*. Rad51 and Dmc1 are the RecA homologs found in eukaryotes, including humans and *Saccharomyces cerevisiae*. RecA/Rad51-like are RecA homologs found in: *Arabidopsis thaliana*, *E. coli*, *Saccharomyces cerevisiae*, *Neurospora crassa*, *Ustilago maydis*, *Sulfolobus solfataricus*, *H. volcanii*, and *M. jannaschii*. RecA/Rad51-like includes Rad51, RecA-like, Sms, Rad57, Rad55, Mei3, Rec2, and RadA. Based on known information, one skilled in the art can thus readily identify the MAW motif in *E. coli* RecA and its homologs.

The MAW mutants listed in FIG. 1 are examples of the mutants of the invention. These mutants exemplify *E. Coli* RecA mutants with one or more mutation sites at positions 47, 49, 53, and 56. The mutants of the invention may have one or more of the mutations indicated.

RecA homolog protein mutants are herein referred to notationally by the residue position at which the replacement is made, the amino acid residue which is replaced, and the replacement residue. For example, replacement of isoleucine (I) by tryptophan (W) at position 49 in *E. coli* is denoted as 49IW. Standard biochemical notations for the amino acids are used. For the same mutation in a homologous protein, the homolog's corresponding RecA MAW amino acid position is used. Further classification is provided by denoting whether a particular mutant is a member of Class V, Class VI, or Class VII, as defined above. For example, the mutation 53AW, named "SuperRecA," is a hyperactive Class V mutant.

Class V mutants are constitutively active RecA homolog protein mutants. Examples of mutants in this class are changes of the alanine at position 53 or changes of the glycines at positions 43, 52, 54, 55, and 59 to volumetrically larger amino acids. The larger amino acids are preferably phenylalanine, lysine, tyrosine, arginine, and tryptophan, with tryptophan being the most preferred replacement amino acid.

Conservation of a protein sequence motif (such as the MAW motif) across all forms of life correlates with a protein structural role or a ligand-binding function. Class V positions are conserved for the protein structural role of enabling the ATP induced conformational change. In wildtype RecA, the MAW motif is buried in the crystal structure which represents the ADP conformation of the RecA protein, that is, closed and less active. ATP or related cofactors induce a conformational change in the RecA protein to an open and active state. The turns in the polypeptide backbone of the MAW motif, for example, at the glycine positions, are involved in this conformational change by acting as flexible hinges. Replacement of glycine or alanine with a volumetrically larger amino acid at the above positions induces the open and active conformation independent of the ATP cofactor. Thus, Class V mutants are constitutively active RecA protein mutants, and therefore ATP-independent. ATP-independence has the dual advantages of reduced cost for processes which currently require ATP or ATPγS and the avoidance of toxicity problems which can arise from use of ATPγS.

Class VI mutants make use of the fact known in the art that the aliphatic-aromatic noncovalent interaction ("interpholation") is weaker than the aromatic-aromatic noncovalent interaction ("intercalation") (E. J. Gabbay et al., Specific Interaction of Peptides with Nucleic Acids, Biochemistry 11:3429–3435 (1972); E. J. Gabbay et al., Specific Interaction of Peptides with Nucleic Acids: Evidence for a Selective Bookmark Recognition Hypothesis", Biochemistry 12:4021–4029 (1973); C. Hélène & J. C. Maurizot, Interactions of Oligopeptides with Nucleic Acids, CRC Crit. Rev. Biochem. 10:213–258 (1981)). As used herein, "interpholation" means aliphatic intercalation.

As mentioned above, conservation of a protein sequence motif (such as the MAW motif) across all forms of life often correlates with a ligand-binding function. In this case the ligand is DNA. The amino acid positions for the Class VI mutant RecA protein (Class VI positions) of the MAW motif are conserved for the role of DNA binding. In the *E. coli* RecA protein, the Class VI positions include residues, such as leucine, isoleucine, threonine and alanine, which interact weakly with DNA via interpholation. Thus, examples of Class VI mutants are: 40IY, 40IW, 42TY, 42TW, 50AY, 50AW, 51LY, and 51LW. The replacement of these residues with aromatic residues, such as tryptophan, would increase the stability of RecA-DNA complexes via intercalation. Aromatic residue replacements include but are not limited to amino acids tryptophan, tyrosine, phenylalanine, and histidine, with tryptophan being the most preferred replacement.

2) Uses of the Invention

*E. coli* RecA protein plays a central role in homologous recombination, post-replication repair, and the SOS response to DNA damage (S. C. West Ann. Rev. Biochem. 61: 603–640 (1992); C. M. Radding J. Biol. Chem. 266: 5355–5358 (1991); A. I. Roca & M. M. Cox, CRC Crit. Rev. Biochem. Molec. Biol. 25: 415–56 (1990)). RecA protein is also a prototype for DNA strand exchange proteins, i.e. recombinases. Purified RecA protein binds cooperatively and stoichiometrically to single-stranded DNA (ssDNA).

In strand exchange, the active species is a nucleoprotein filament containing one RecA monomer (38 kDa) per 3 bases of ssDNA. ATP hydrolysis is not required for filament formation or pairing to duplex DNA (dsDNA). However, ATP hydrolysis is required for unidirectional DNA strand exchange, dissociation of the protein, bypass of structural barriers in DNA, and 4-strand exchange reactions. One of the more useful commercial properties of RecA is its ability to locate and pair a ssDNA sequence to its homologous dsDNA sequence in the presence of ATPγS or ATP. This behavior has been exploited to enrich for specific DNA sequences (B. Taidi-Laskowski, et al., Nucl. Acids Res. 16:8157 (1988); S. M. Honigberg, et al., Proc. Nat. Acad. Sci. U.S.A. 83: 9586 (1986); B. Rigas, et al., Proc. Nat. Acad. Sci. U.S.A. 83:9591 (1986)) and to protect specific DNA sites from methylation or endonuclease cleavage. (L. J. Ferrin & R. D. Camerini-Otero, Science 254:1494 (1991); M. Koob, et al., Nucleic Acids Res 20:5831 (1992)) For example, RecA protein is commonly used in the following applications:

(1) Enrichment method for genomic cloning (Taidi-Laskowski (1988), supra; Honigberg (1986), supra; and Rigas (1986), supra;

(2) Sequence specific cleavage of large segments of DNA, for example, RecA-assisted restriction endonuclease (RARE), Achilles' heel cleavage, Ferrin (1991) and Koob (1992), supra;

(3) D-loop mutagenesis (D. Shortle, et al., Proc. Nat. Acad. Sci. U.S.A. 77:5375 (1980));

(4) Coating of DNA with RecA protein to enhance contrast of electron micrographs (M. A. Krasnow, et al., Nature 304: 559 (1983));

(5) Isothermal DNA amplification (U.S. Pat. No. 5,223, 414, Process for Nucleic Acid Hybridization and Amplification, Jun. 29, 1993, to D. A. Zarling, et al.); and (6) Gene therapy (U.S. Pat. No. 5,719,023, In Situ Hybridization Method, Feb. 17, 1998, to D. A. Zarling, et al.).

Other applications of the RecA protein are disclosed in the patents referenced above. The RecA mutant protein of the present invention can replace the wildtype RecA protein or other non-MAW RecA mutants in the above described five applications and the applications described in the referenced patents. Because these are RecA mutants, they may be used under similar conditions as disclosed in the above applications and patents. One skilled in the art would be able to, without undue experimentation, make any modifications necessary to accommodate the mutants.

A current limitation of using the wildtype RecA protein (commercially available from Promega, Pharmacia, and New England Biolabs) or other non-MAW RecA mutants is the need to use a nucleotide cofactor, such as ATPγS. This non-hydrolyzable analog of ATP locks the RecA protein into an active conformation for DNA binding and/or homology search. ATPγS is expensive and not a common reagent for molecular biology laboratories. Further, isothermal DNA amplification using the wildtype RecA protein is limited in the selection of DNA polymerases that can be used. Current technology can only use polymerases that are not inhibited by ATPγS. ATPγS may be toxic for in vivo applications.

The invention defines an ATP conformational switch and a DNA binding site of the RecA homolog protein (the MAW motif), and provides for a method for producing mutants in this region to circumvent the need for ATPγS. In vivo results of the SuperRecA mutant (53AW) suggest that this mutation is a constitutive RecA mutant with respect to DNA binding. (See A. I. Roca, Initial Characterization of Mutants in a Universally Conserved RecA Structural Motif, Doctoral Thesis, University of Wisconsin, Madison, Wis. (1997) and FIG. 2).

The mutants in the MAW motif of the invention, in which Class V mutants (such as SuperRecA) are novel ATP-independent RecA homolog protein mutants, enable the applications which traditionally use RecA protein to be performed with greater ease and less expensively, for example, by not requiring ATPγS. Further, in the isothermal DNA amplification, the use of SuperRecA will allow other DNA polymerases and associated processivity factors which may improve DNA amplification results. Therefore, the MAW mutants may replace current technology and expand the RecA market. Because these are mutants of RecA protein, they may be used under similar conditions as the wildtype or non-MAW mutant RecA proteins in its traditional applications.

Class VI RecA protein mutants, due to their stronger (compared to wildtype RecA protein) binding to DNA, are useful in any applications which use wildtype RecA protein (or other RecA mutants with a wildtype MAW motif sequence) which would be improved by having a stronger DNA binding RecA protein mutant. Such applications which may be improved include the uses of RecA protein coated single-stranded DNA in gene targeting/therapy technology. Methods for using wildtype RecA protein-mediated homologous DNA targeting in vivo are found in S. C. Kowalczykowski & D. A. Zarling, in Gene Targeting, M. A. Vega, Ed., CRC Press, Inc., Boca Raton, FL, pp. 167–210 (1994) and U.S. Pat. No. 5,763,240, In Vivo Homologous Sequence Targeting in Eukaryotic Cells, Jun. 9, 1998, to D. A. Zarling & E. P. Sena The goal of gene targeting/therapy is to use RecA to catalyze homologous pairing of an exogenous single-stranded DNA to its targeted endogenous homologous double-stranded DNA in vivo. The conditions used to coat targeting polynucleotides with RecA proteins and ATPγS have been described in U.S. patent application Ser. No. 07/755,462 filed Sep. 4, 1991 and U.S. patent application Ser. No. 07/520,321, filed May 7, 1990.

By providing a more stable mutant RecA protein coated DNA strand, the invention decreases the chance of or prevents the dissociation of the RecA protein from the DNA stand before reaching the targeted DNA within the cell nucleus.

RecA protein mutants of the invention were produced in accordance with the procedures of Example 1.

EXAMPLE 1

Creation of RecA Homolog Protein Mutants

1) Bacterial strains and molecular biology reagents

Bacterial strains and plasmids are listed in Tables 1 and 2, respectively. Strain STL2669, a gift of Susan Lovett (Brandeis University), is an unpublished recA deletion exo I⁻ strain used for purifying RecA mutants. This strain is available to the public on written request to Dr. Lovett.

TABLE 1

Bacterial Strains

| Strain | Genotype | Source |
|---|---|---|
| AIR4 | ompT hsdSB gal dcm lon Δ(srl-recA)306::Tn10 | † |
| CJ236 | dut-1 ung-1 thi-1 relA-1 [F' pCJ105] | Bio-Rad Labs |
| DE1663' | Δ(recA-srlR)306::Tn10 Δ(lac-argF)U169 sulA211 malB::Tn9 thr leu his pro arg lac gal ara xyl mtl [F' lacI$^Q$ lacPL8 lacZ4505::Tn5 proA$^+$B$^+$] [λcI ind-1 recAo/p::lacZY] | †† |
| JM109 | e14 (McrA) Δ(lac-proAB) thi gyrA96 endA1 hsdR17 relA1 supE44 recA1 [F traD36 proA$^+$B$^+$ laqI$^Q$ Δ(lacZ)M15] | Promega Corp. |
| STL2669 | thr-1 leuB6 proA62F gpt62F supE44 kdgK51 rfbD1 ara-14 lacY1 gal/K2 xyl-5 mtl-1 tsx-33 rpsL31 xonA2 (sbcB$^-$) Δ(recA-sr/R)306::Tn10 | S. Lovett |

† A. I. Roca, initial Characterization of Mutants in a Universally Conserved RecA Structural Motif, Doctoral Thesis, University of Wisconsin, Madison, WI (1997)
†\ J. T. Konola, H. G. Nastri, K. M. Logan & K. L. Knight, Mutations at Pro$^{67}$ in the RecA Protein P-Loop Motif Differentially Modify Coprotease Function and Separate Coprotease from Recombination Activities, J. Biol. Chem. 270:8411–9 (1995)

TABLE 2

Bacterial Plasmids

| Plasmid | Description | Source |
|---|---|---|
| pAIR42 | subclone of recA amino terminal coding region for in vitro mutagenesis | † |
| pAIR50's | subclone of recA amino terminal coding region with MAW mutations | †, see Table 3, below |
| pAIR70's | MAW mutant recA constructs for in vivo assays | †, see Table 3, below |
| pAIR79 | wildtype RecA overexpression construct | † |
| pAIR80's | MAW mutant RecA overexpression constructs | †, see Table 3, below |
| pT7POL26 | T7 RNA Polymerase delivery plasmid | †† |
| pTRecA103 | source of recA N-terminal coding region lacking internal NcoI site | ††† |
| pTRecA220 | wildtype recA construct for in vivo assays | †††† |
| pZ150 | parent vector of pTRecA220 | ††† |

† A. I. Roca, Initial Characterization of Mutants in a Universally Conserved RecA Structural Motif, Doctoral Thesis, University of Wisconsin, Madison, WI (1997)
†† N. Mertens, E. Remaut & W. Friers, Tight Transcriptional Control Mechanism Ensures Stable High-Level Expression from T7 Promoter-based Expression Plasmids, Bio/Technology 13:175–9 (1995)
††† K. M. Logan & K. L. Knight, Mutagenesis of the P-loop Motif in the ATP Binding Site of the RecA Protein from *Escherlchia coli*, J. Mol. Biol. 232:1048–59 (1993)
†††† M. C. Skiba & K. L. Knight, Functionally Important Residues at a Subunit Interface Site in the RecA Protein from *Escherichia coli*, J. Biol. Chem. 269:3823–8 (1994)

*E. coli* cultures were grown at 37° C. in either liquid or solid LB medium (See J. Sambrook, E. F. Fritsch & T. Maniatis, *Molecular Cloning: A Laboratory Manual* (Cold Spring Harbor Laboratory, Cold Spring Harbor, N.Y., 2d ed. 1989)) with the following antibiotic (Sigma) concentrations when appropriate: ampicillin (100 μg/ml); kanamycin (40 μg/ml); tetracycline (15 μg/ml); chloramphenicol (25 μg/ml). Restriction endonucleases were from New England Biolabs. Deoxyadenosine 5'-[α-[$^{35}$S]triphosphate and Sequenase were from Amersham/United States Biochemicals. Deoxyoligonucleotides were obtained from Research Genetics (Huntsville, Ala.). Isopropyl-β-D-thiogalactoside ("IPTG"), mitomycin C ("MMC"), and o-nitrophenyl β-D-galactopyranoside ("ONPG") were from Sigma. Bradford reagent was from Bio-Rad Labs.

2) Construction of MAW Mutants

A subclone of the wildtype recA ORF encoding only the amino-terminal region of the RecA protein (from the start codon to the unique PstI site, 237 bp) was used for mutagenesis. Plasmid pTRecA103 was used as the source of the subclone since the relevant region of the recA gene had already been modified to make the gene more amenable to subsequent cloning manipulations. First, a silent NcoI site had been introduced at the recA start codon to allow swapping of the amino-terminal region of the recA gene between plasmids. Second, a silent mutation was introduced within the amino terminal region to destroy an internal NcoI site that would have interfered with cloning. (See K. M. Logan & K. L. Knight, Mutagenesis of the P-loop Motif in the ATP Binding Site of the RecA Protein from *Escherichia coli*, J. Mol. Biol. 232:1048–59 (1993)). This region of the recA gene was PCR amplified (See K. Mullis & F. A. Faloona, Specific Synthesis of DNA in vitro Via a Polymerase-catalyzed Chain Reaction, Methods Enzymol. 155:335–50 (1987)) using an upstream primer complementary to the start codon of recA and downstream sequences. This primer also introduced a BamHI site upstream of the start codon for cloning purposes. The downstream primer was complementary to the PstI region of the RecA gene. Standard procedures (See J. Sambrook, E. F. Fritsch & T. Maniatis, *Molecular Cloning: A Laboratory Manual* (Cold Spring Harbor Laboratory, Cold Spring Harbor, N.Y., 2d ed. 1989)) were used to clone the BamHI to PstI PCR product into pGEM3Zf (–) using the same restriction sites to create plasmid pAIR42. Both strands of the subclone were sequenced to ensure that no errors were introduced during the PCR reaction. Dideoxy sequencing (See F. Sanger, S. Nicklen & A. R. Coulson, DNA Sequencing With Chain-terminating inhibitors, Proc. Nat. Acad. Sci., U.S.A. 74:5463–7 (1977)) of the double-stranded template (Magic Mini-prep DNA purification system, Promega) was performed using modified T7 DNA polymerase (Sequenase) and commercially available primers (Promega) as described (United States Biochemicals).

Plasmid pAIR42 (See A. I. Roca, Initial Characterization of Mutants in a Universally Conserved RecA Structural Motif, Doctoral Thesis, University of Wisconsin, Madison, Wis. (1997)) was used as the template for oligo-directed mutagenesis (See C. S. Craik, Use of Oligonucleotides for Site-Specific Mutagenesis, BioTech. 12–9 (1985)) using the Kunkel selection method (See T. A. Kunkel, J. D. Roberts & R. A. Zakour, Rapid and Efficient Site-specific Mutagenesis without Phenotypic Selection, Methods Enzymol. 154:367–82 (1987)) as supplied in the Muta-Gene Phagemid in vitro mutagenesis kit (Bio-Rad). Briefly, uracil-containing ssDNA of pAIR42 was made using strain CJ236.Synthetic oligonucleotides coding for the desired MAW mutation and, if possible, a nearby silent restriction endonuclease site change were annealed to the template in vitro. DNA polymerization and ligation reactions were performed with T4 DNA polymerase and T4 DNA ligase, respectively (Bio-Rad). Mutagenesis reactions were electroporated into strain JM109 using a Bio-Rad Gene-Pulser as described by the manufacturer. Transformants were screened by diagnostic restriction digests and dsDNA sequencing. The mutations created and their respective plasmid clones are listed in Table 3. Both strands of the amino terminal MAW mutant subclones (pAIR50's) were sequenced as described above. No errors were detected. Care must be taken in the design of the mutagenesis oligonucleotides and the screening of isolated mutations by sequencing. This region of the recA gene is rich in guanines and cytosines that can introduce artifacts in these procedures. In particular, the introduction of a tryptophan codon can exacerbate the GC-richness problem since it is encoded by only one codon (TGG).

TABLE 3

MAW Mutants and Their Respective Plasmid Clones

| RecA aa position | wildtype aa (code) | mutant aa | Nterm subclone | in vivo assay clone | overexpression clone |
|---|---|---|---|---|---|
| — | — | — | pAIR42 | pTRecA220 | pAIR79 |
| 47 | leu (L) | trp (W) | pAIR50 | pAIR70 | pAIR80 |
| 47 | leu | tyr (Y) | pAIR51 | pAIR71 | pAIR81 |
| 49 | ile (I) | trp | pAIR55 | pAIR75 | pAIR85 |
| 53 | ala (A) | trp | pAIR56 | pAIR76 | pAIR86 |
| 56 | leu | trp | pAIR52 | pAIR72 | pAIR82 |
| 56 | leu | tyr | pAIR53 | pAIR73 | pAIR83 |

Full length recA clones containing the MAW mutants were then created (See Table 3). Separate plasmid clones were constructed for the in vivo assays (pAIR70's) and overexpression system pAIR80's). The in vivo assay plasmid pTRecA220 encoding the full length wildtype recA gene was used as the backbone for carrying the different MAW mutants. For example, the NcoI to PstI fragment carrying the MAW mutation 47LY from pAIR51 was swapped for the NcoI-PstI wildtype coding region of pTRecA220 to create pAIR71. The in vivo assay plasmids were electroporated into E. coli strain DE1663'. In a similar manner, the MAW mutations were moved into the overexpression plasmid pAIR79 and kept in strain AIR4 or STL2669. Hence, the plasmid used to overexpress the MAW mutant 47LY is pAIR81.

RecA protein expression from the pTRecA220 vector is regulated by a tac promoter. It has been determined that in the absence of inducer, RecA protein levels from this construct are ≈20X higher than the base level of expression from a chromosomal copy of the recA gene (See M. C. Skiba & K. L. Knight Functionally Important Residues at a Subunit Interface Site in the RecA Protein from *Excherichia coli*, J. Biol. Chem. 269:3823–8 (1994)).

EXAMPLE 2

In Vivo Results With RecA Mutant 53AW

LexA cleavage assay

Strain DE1663' carries the lacZ gene under the control of the LexA-regulated recA promoter. Therefore, the measurement of β-galactosidase activity is related to the extent of RecA-mediated LexA cleavage. The following quantitative cell extract assay was performed essentially as described (See Konola, et al., J. Biol. Chem. 270:8411 (1995)) with the following modifications. Single colonies from a freshly streaked plate were used to inoculate overnight cultures. A 1:100 subculture was grown for ≈2 hours. The cultures were divided in half with one half brought to a final to concentration of 0.5 μg/ml mitomycin C ("MMC"). MMC is a DNA damaging agent which will activate the RecA protein and subsequent SOS response in vivo. The incubation was continued for 3 hours, then the cultures were chilled on ice for 20 min. Cells were pelleted by centrifugation at 4° C. Cells were resuspended in Z buffer (See Miller, in *A Short Course in Bacterial Genetics: A Laboratory Manual and Handbook for Escherichia coli and Related Bacteria*, Cold Spring Harbor Laboratory Press, Cold Spring Harbor, N.Y., 1992,p. 43) and kept on ice. Cells were lysed by sonication for ≈30 sec at 30 Watts using a Branson Sonifer model 450, centrifuged, and stored at 4° C. The β-galactosidase activity in the clarified supernatants was determined using ONPG as described ((See Miller, in *A Short Course in Bacterial Genetics: A Laboratory Manual and Handbook for Escherichia coli and Related Bacteria*, Cold Spring Harbor Laboratory Press, Cold Spring Harbor, N.Y., 1992,p. 43). The same extracts were also used for Bradford assays and therefore the units of activity are defined as $OD_{420} \times vol_{595}/(time \times vol_{420} \times OD_{595})$. The $OD_{420}$ and $OD_{595}$ are read from the β-galactosidase or Bradford reaction mixture, respectively. "Time" refers to the time of the β-galactosidase reaction in minutes. "Vol" refers to the volume of the culture (in milliliters) used in the assay for either the β-galactosidase or Bradford reaction. This unit definition differs from both the classical "Miller" units (See Miller, in *A Short Course in Bacterial Genetics: A Laboratory Manual and Handbook for Escherichia coil and Related Bacteria*, Cold Spring Harbor Laboratory Press, Cold Spring Harbor, N.Y., 1992,p. 43) as well as the protocol from which these strains were taken (See Konola, et al, J. Biol. Chem. 270:8411 (1995)). Extract from the control strain DE1663' pTRecA220 was prepared fresh along with samples for each experiment. It has been determined that a 3 hour incubation time after MMC treatment yields maximal assay activity with this strain and plasmid combination (See Konola, et al., J. Biol. Chem. 270:8411 (1995)). The experiment was repeated three times for each mutant examined.

Results of the experiments are reflected in FIG. 2. FIG. 2 shows results using E. coli strain DE1663' (recA deletion) transformed with plasmids expressing the MAW mutants 47LW, 47LY, 56LW, 56LY, 49IW, and 53AW, wildtype RecA, and parent vector (pZ150), which were assayed as described above for β-galactosidase activity. Cultures were assayed in the absence or presence (shaded) of 0.5 μg/ml mitomycin C as indicated. Note that, in the presence of MMC, RecA activity increases for the wildtype and mutant proteins except for 47LY. In the absence of RecA or with a defective mutant (i.e., 47LY), only background levels of activity are observed after MMC treatment. The hyperactive SuperRecA mutant (53AW) displays activity in the absence of DNA damage. Units are defined as the ratio of absorbance (420/595 nm) readings from the β-galactosidase and Bradford assays. Values are the average of three experiments and the standard error is indicated in the figure.

EXAMPLE 3

Purification of RecA Mutant 49IW

1) Overexpression and Fermentation

A derivative of E. coli strain BL21 (Novagen) was created to remove the chromosomal recA gene. This would prevent the wildtype RecA protein from contaminating MAW mutant protein preparations. The construction of this new strain, AIR4, is described in A. I. Roca, Initial Characterization of Mutants in a Universally Conserved RecA Structural Motif, Doctoral Thesis, University of Wisconsin, Madison, Wis. (1997), Appendix 2. The MAW mutant overexpression constructs have the appropriate ORF with no junction cloning artifacts inserted into the pET21d vector (Novagen, Madison, Wis.). Thus, transcription is controlled by the T7 RNA polymerase (RNAP) from the T7 Ø10 promoter (See Studier, et al., Methods Enzymol. 185:60 (1990)). The T7 RNAP is delivered by a separate plasmid, pT7POL26, which tightly regulates transcription of T7 RNAP via IPTG induction (See Mertens, et al., Bio/Technology 13:175 (1995)).

Overexpression of MAW mutants using a fermenter were generally performed in the following manner. A single colony from freshly electroporated cells (strain AIR4) was used to inoculate a 30 ml culture of LB with a high antibiotic selection of 400 μg/ml ampicillin and 40 μg/ml kanamycin for overnight incubation in a shaken flask. The cells from the saturated culture were pelleted and resuspended in fresh LB with antibiotics. The resuspended cells were used to subculture 500 ml of the same medium at a starting $OD_{600}$ of ~0.1. The culture $OD_{600}$ was closely monitored until a value of ≈0.5 was reached. This subculture was then used to inoculate 5 liters of TB (See Sambrook, et al., Molecular Cloning: A Laboratory Manual, Cold Spring Harbor Laboratory, Cold Spring Harbor, N.Y., ed. 2nd, 1989)) without antibiotic selection in a New Brunswick Bioflo 3000 bench top fermenter. The following parameters on the fermenter were used: temperature 37° C., pH≈7.5, air flow 30 liters/min, dissolved oxygen 20%, and automatic agitation (200–800 rpm) was set to maintain the desired DO level. When the $OD_{600}$ reached ≈5–15, the culture was induced with a final concentration of 0.2% lactose. Incubation was continued for another 5 hours before cells were harvested with a Millipore filtration system using a Masterflex Pump and a Pellicon Cassette. The final $OD_{600}$ was ≈10–40 with a wet cell mass weighing ≈150 grams. The cells were quick frozen in liquid nitrogen and stored at −70° C.

An ExoI nuclease deficient strain, STL2669, was also used to overproduce the MAW mutants. Fermenter conditions were similar to the above description except for the following changes. A New Brunswick Scientific 60 liter Mobile Pilot Plant fermenter was inoculated with an exponential phase 3 liter subculture of bacteria. The culture in the fermenter was induced at an $OD_{600}$ of 0.5 with 0.1 mM IPTG and outgrown for 3 hours. Cells were harvested with a Sharples continuous flow centrifuge. The final $OD_{600}$ was ≈1 yielding a wet cell mass of ≈200 grams. Protein overexpression was induced at a lower $OD_{600}$ than above to minimize plasmid loss that is problematic in nuclease deficient strains (See Bassett & Kushner, J. Bateriol. 157:661 (1984)).

2) Biochemical Reagents

The protein concentration of the purified RecA49IW MAW mutant was determined by absorbance at 280 nm using a theoretical extinction coefficient of $\epsilon_{280}$=0.71 $A_{280}$ ml/mg and a calculated molecular weight of 37,919. The extinction coefficient was calculated using previously determined parameters for tyrosines and tryptophans. (See C. N. Pace, F. Vajdos, L. Fee, G. Grimsley, and T. Gray, How to Measure and Predict the Molar Absorption Coefficient of a Protein, Protein Science 4:2411–23 (1995)). DEAE-Sepharose FF resin was from Pharmacia Biotech, Inc. Hydroxyapatite BioGel HTP resin was from Bio-Rad. The prepacked Poros HQ/P column was from PerSeptive Biosystems. ATP, polyethyleneimine, and Tris were from Sigma. Ammonium sulfate ("AmS"), potassium chloride, and potassium phosphate were from Fisher. Dithiothreitol was from Research Organics.

3) Buffers

P buffer contained 20 mM potassium phosphate 50% dianion (pH 6.8 at 25° C.), 1 mM dithiothreitol ("DTT"), 0.1 mM ethylenediaminetetraacetic acid ("EDTA"), 10% (w/v) glycerol. R buffer contained 20 mM Tris-HCl 80% cation (pH 7.5), 1 mM DTT, 0.1 mM EDTA, 10% (w/v) glycerol. Buffers were made from 20X concentrated stocks.

4) Purification

Purification of RecA 49IW was accomplished essentially as described (See M. M. Cox, K. McEntee & I. R. Lehman, A Simple and Rapid Procedure for the Large Scale Purification of the RecA Protein of *Escherichia coli*, J. Biol. Chem. 256:4676–8 (1981); Q. Shan, M. M. Cox & R. B. Inman, DNA Strand Exchange Promoted by RecA K72R: Two Reaction Phases with Different $Mg^{2+}$ Requirements, J. Biol. Chem. 271:5712–24 (1996)) with modifications. All steps were carried out at 4° C. A 20% (w/v) suspension of thawed STL2669 fermenter cells (8 g) in sucrose solution was lysed with a Gaulin Laboratory Homogenizer model 15M-8TA using 3 passes at a pressure of 10,000 pounds per square inch. The lysate was clarified using a Beckman 60Ti rotor spun at 40,000 rpm for 45 min at 4° C. The supernatant was adjusted to an $OD_{260}$ of ≈160 as previously described (See S. Tateishi, T. Horii, T. Ogawa & H. Ogawa, C-terminal Truncated *Escherichia coli* RecA Protein RecA5327 has Enhanced Binding Affinities to Single-stranded and Double-stranded DNAs, J. Mol. Biol. 223:115–29 (1992)) to create fraction I (115 ml). Polyethyleneimine (5% w/v, pH 7.5) was added to fraction I to a final concentration of 0.5%. The suspension was stirred for 30 min and then centrifuged for 15 min at 9000 rpm in a Beckman JA14 rotor. The pellet was washed with R buffer+150 mM AmS. The suspension was stirred and centrifuged as before. The mutant RecA protein was extracted from the pellet with R buffer+300 mM AmS after stirring and centrifugation. This RecA-containing supernatant was set aside. The pellet was re-extracted with the same AmS solution as before. The supernatant were combined and solid AmS (0.28 g/ml) was slowly added. The suspension was left to stir overnight. The suspension was centrifuged at 13,000 rpm for 30 min using the JA14 rotor. The pellet was washed with R buffer+0.28 g/ml AmS and centrifuged as before. This wash was repeated two more times. The final pellet was gently resuspended in R buffer+50 mM KCl and dialyzed against 3×1 liter of the same buffer to generate fraction II (32 ml, 330 mg of protein).

Fraction II was loaded at a protein concentration of ≈5 mg/ml onto a DEAE-Sepharose FF column (2.5×16 cm) equilibrated in R buffer+50 mM KCl. The column was washed with R buffer+50 mM KCl at a linear velocity of 13 cm/h. Mutant RecA protein was monitored by SDS-PAGE. The pooled flow through protein peak (fraction III, 49 ml, 125 mg protein) was loaded directly onto a hydroxyapatite column (2.5×11.5 cm) pre-equilibrated in P buffer at a protein concentration of 2.5 mg/ml as previously described (See T. Shibata, R. P. Cunningham & C. M. Radding, Homologous Paring in Genetic Recombination: Purification and Characterization of *Escherichia coli* RecA Protein, J. Biol. Chem. 256:7557–64 (1981)). The column was washed extensively with P buffer and developed with a 10 column volume phosphate gradient from 20 to 200 mM at a linear velocity of 17 cm/h. Nuclease free fractions were pooled and dialyzed against 3×1 liter of R buffer+50 mM KCl to generate fraction IV (130 ml, 64 mg protein). Fraction IV was applied to a 0.8 ml Poros HQ/P FPLC column for several runs using a superloop. The column was washed with 3 ml R+50 mM KCl buffer and then developed with 15 ml of 0.05 to 2 M KCl linear gradient. Peak fractions were pooled and dialyzed against 2×2 liters of R buffer to yield the final fraction V (8.4 ml, 45 mg protein). Aliquots of the fraction were frozen in liquid nitrogen and stored at −70° C. in different freezers. The RecA 49IW mutant protein was at least 99% pure as judged by a densitometric scan of a Coomassie Blue-stained SDS-PAGE gel that was loaded with ≈25 μg of protein. The concentration of the mutant was determined using the extinction coefficient described above. This particular protein preparation was free of detectable endo- or exonucleases.

Figure 3:
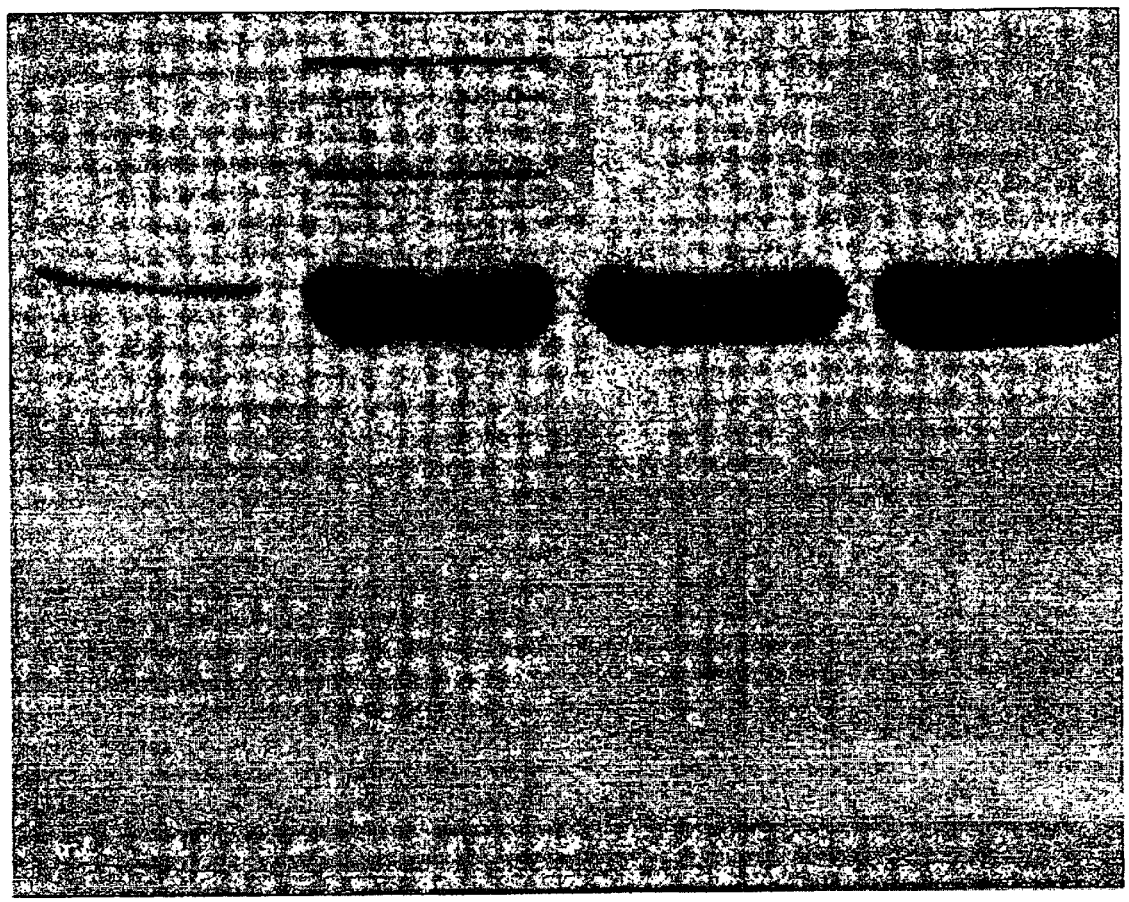
FIG. 3 is the SDS-PAGE visualization of purified MAW mutant RecA 49IW, giving a comparison of each major fraction (25 μg) from the STL2669 strain 49IW preparation.

FIG. 3 shows the SDS-PAGE visualization of purified MAW mutant RecA 49IW, giving a comparison of each major fraction (25 μg) from the STL2669 strain 49IW preparation. The four fractions shown in FIG. 3 are:

I. Clarified lysate.

II. The 300 mM AmS extraction from the polyethyleneimine pellet.

III. The flowthrough from the DEAE-Sepharose column.

IV. The concentrated pool from the phosphate gradient peak off the hydroxyapatite column.

Those skilled in the art will understand that the descriptions above allow the use of other purification methods, such as by modifying the methods found in S. M. Cotterill, et al., Biochemistry 21: 4332 (1982); M. M. Cox, et al., J. Biol. Chem. 256: 4676 (1981); T. Shibata, et al., J. Biol. Chem. 256: 7557 (1981); J. Griffith & C. G. Shores, Biochemistry 24: 158 (1985); and Q. Shan, et al., J. Biol. Chem. 271: 5712 (1996). Although the invention has been described in detail by way of illustration and example for purposes of clarity and understanding, modifications, and changes which are within the skill of those skilled in the art are considered to fall within the scope of the invention.

I claim:

1. A purified mutant RecA protein comprising SEQ ID NO: 3 and having an enhanced DNA binding activity compared to an unmutated RecA protein from the same source, wherein a naturally occurring amino acid residue, located within said sequence, is replaced with an amino acid residue which is volumetrically larger than the replaced amino acid residue.

2. The purified mutant RecA protein of claim 1, wherein said replacement occurs at residue 4 of SEQ ID NO: 3.

3. The purified mutant RecA protein of claim 1, wherein said replacement occurs at residue 13 of SEQ ID NO: 3.

4. The purified mutant RecA protein of claim 1, wherein said replacement occurs at residue 14 of SEQ ID NO: 3.

5. The purified mutant RecA protein of claim 1, wherein said replacement occurs at residue 15 of SEQ ID NO: 3.

6. The purified mutant RecA protein of claim 1, wherein said replacement occurs at residue 16 of SEQ ID NO: 3.

7. The purified mutant RecA protein of claim 1, wherein said replacement occurs at residue 20 of SEQ ID NO: 3.

8. The purified mutant RecA protein of claim 1, wherein said replacement amino acid residue is selected from the group of phenylalanine, lysine, tyrosine, arginine, and tryptophan.

9. The purified mutant RecA protein of claim 2, wherein said replacement amino acid residue is selected from the group of phenylalanine, lysine, tyrosine, arginine, and tryptophan.

10. The purified mutant RecA protein of claim 3, wherein said replacement amino acid residue is selected from the group of phenylalanine, lysine, tyrosine, arginine, and tryptophan.

11. The purified mutant RecA protein of claim 4, wherein said replacement amino acid residue is selected from the group of phenylalanine, lysine, tyrosine, arginine, and tryptophan.

12. The purified mutant RecA protein of claim 5, wherein said replacement amino acid residue is selected from the group of phenylalanine, lysine, tyrosine, arginine, and tryptophan.

13. The purified mutant RecA protein of claim 6, wherein said replacement amino acid residue is selected from the group of phenylalanine, lysine, tyrosine, arginine, and tryptophan.

14. The purified mutant RecA protein of claim 7, wherein said replacement amino acid residue is selected from the group of phenylalanine, lysine, tyrosine, arginine, and tryptophan.

15. A purified mutant RecA protein comprising SEQ ID NO: 3 and having an enhanced DNA binding activity compared to an unmutated RecA protein from the same source, wherein a naturally occurring amino acid residue, located within said sequence, but excluding residues 8 and 12 of SEQ ID NO: 3, is replaced with an aromatic amino acid residue.

16. The purified mutant RecA protein of claim 15, wherein said replacement occurs at residue 1 of SEQ ID NO: 3.

17. The purified mutant RecA protein of claim 15, wherein said replacement occurs at residue 3 of SEQ ID NO: 3.

18. The purified mutant RecA protein of claim 15, wherein said replacement occurs at residue 5 of SEQ ID NO: 3.

19. The purified mutant RecA protein of claim 15, wherein said replacement occurs at residue 11 of SEQ ID NO: 3.

20. The purified mutant RecA protein of claim 15, wherein said replacement occurs at residue 17 of SEQ ID NO: 3.

21. The purified mutant RecA protein of claim 15, wherein said replacement amino acid residue is selected from the group of tryptophan, tyrosine, phenylalanine, and histidine.

22. The purified mutant RecA protein of claim 16, wherein said replacement amino acid residue is selected from the group of tryptophan tyrosine, phenylalanine, and histidine.

23. The purified mutant RecA protein of claim 17, wherein said replacement amino acid residue is selected from the group of tryptophan, tyrosine, phenylalanine, and histidine.

24. The purified mutant RecA protein of claim 18, wherein said replacement amino acid residue is selected from the group of tryptophan tyrosine, phenylalanine, and histidine.

25. The purified mutant RecA protein of claim 19, wherein said replacement amino acid residue is selected from the group of tryptophan, tyrosine, phenylalanine, and histidine.

26. The purified mutant RecA protein of claim 20, wherein said replacement amino acid residue is selected from the group of tryptophan, tyrosine, phenylalanine, and histidine.

27. A purified mutant RecA protein comprising SEQ ID NO: 3 and having an enhanced DNA binding activity compared to an unmutated RecA protein from the same source, wherein a naturally occurring amino acid residue located at residues 8 or 12 of SEQ ID NO: 3, is replaced with a tryptophan residue.

* * * * *

SEQUENCE LISTING

```
<160> NUMBER OF SEQ ID NOS: 3

<210> SEQ ID NO 1
<211> LENGTH: 26
<212> TYPE: PRT
<213> ORGANISM: Escherichia coli
<220> FEATURE:
<221> NAME/KEY: NON_TER
<222> LOCATION: (1)
<220> FEATURE:
<221> NAME/KEY: NON_TER
<222> LOCATION: (26)..)
<220> FEATURE:
<221> NAME/KEY: HELIX
<222> LOCATION: (6)..(12)
<223> OTHER INFORMATION: Alpha-helix B
<220> FEATURE:
<221> NAME/KEY: STRAND
<222> LOCATION: (22)..(26)
<223> OTHER INFORMATION: Beta-strand 1
<220> FEATURE:
<221> NAME/KEY: SIMILAR
<222> LOCATION: (1)..(26)
<223> OTHER INFORMATION: This structure is highly conserved across
      bacterial RecA and homologous eukaryotic,
      archaeal, and viral  proteins;  sequence below is
      from E. coli RecA positions 40-65

<400> SEQUENCE: 1

Ile Ser Thr Gly Ser Leu Ser Leu Asp Ile Ala Leu Gly Ala Gly Gly
 1               5                  10                  15

Leu Pro Met Gly Arg Ile Val Glu Ile Tyr
            20                  25

<210> SEQ ID NO 2
<211> LENGTH: 26
<212> TYPE: PRT
<213> ORGANISM: Escherichia coli
<220> FEATURE:
<221> NAME/KEY: NON_TER
<222> LOCATION: (1)
<220> FEATURE:
<221> NAME/KEY: NON_TER
<222> LOCATION: (26)
<220> FEATURE:
<221> NAME/KEY: HELIX
<222> LOCATION: (6)..(12)
<223> OTHER INFORMATION: Alpha-helix B
<220> FEATURE:
<221> NAME/KEY: STRAND
<222> LOCATION: (22)..(26)
<223> OTHER INFORMATION: Beta-strand 1
<220> FEATURE:
<221> NAME/KEY: SIMILAR
<222> LOCATION: (1)..(26)
<223> OTHER INFORMATION: Non 'Xaa' residues are the invariant MAW-motif
      residues in RecA and its homologs
<220> FEATURE:
```

-continued

```
<221> NAME/KEY: SITE
<222> LOCATION: (1)
<223> OTHER INFORMATION: This site is not invariant across RecA homologs
      and has observed to contain Ile, Phe, Met, Thr,
      Val, Tyr, or Leu
<220> FEATURE:
<221> NAME/KEY: SITE
<222> LOCATION: (2)
<223> OTHER INFORMATION: This site is not invariant across RecA homologs
      and has been observed to contain Ser, Gly, Lys,
      Pro, Thr, or Arg
<220> FEATURE:
<221> NAME/KEY: SITE
<222> LOCATION: (3)
<223> OTHER INFORMATION: This site is not invariant across RecA homologs
      and has been observed to contain Thr, Ser, or Trp
<220> FEATURE:
<221> NAME/KEY: SITE
<222> LOCATION: (4)
<223> OTHER INFORMATION: This site is not invariant across RecA homologs
      and has been observed to contain Gly, Arg, Ala,
      Lys, Asn, or Gln
<220> FEATURE:
<221> NAME/KEY: SITE
<222> LOCATION: (5)
<223> OTHER INFORMATION: This site is not invariant across RecA homologs
      and has been observed to contain Ser, Ala, Cys,
      Ile, Asn, Asp, or Phe
<220> FEATURE:
<221> NAME/KEY: SITE
<222> LOCATION: (6)
<223> OTHER INFORMATION: This site is not invariant across RecA homologs
      and has been observed to contain Leu, Ile, Thr,
      Val, Tyr, Lys, Gln, Asp, Pro, or Arg
<220> FEATURE:
<221> NAME/KEY: SITE
<222> LOCATION: (7)
<223> OTHER INFORMATION: This site is not invariant across RecA homologs
      and has been observed to contain Ser, Ala, Asp,
      Gly, Leu, Met, Thr, Val, Tyr, Glu, Asn, or Gln
<220> FEATURE:
<221> NAME/KEY: SITE
<222> LOCATION: (8)
<223> OTHER INFORMATION: This site is not invariant across RecA homologs
      and has been observed to contain Leu, Ile, Val,
      Phe, or Met
<220> FEATURE:
<221> NAME/KEY: SITE
<222> LOCATION: (9)
<223> OTHER INFORMATION: This site is not invariant across RecA homologs
      and has been oberved to contain Asp or Asn
<220> FEATURE:
<221> NAME/KEY: SITE
<222> LOCATION: (10)
<223> OTHER INFORMATION: This site is not invariant across RecA homologs
      and has been observed to contain Ile, Ala, Glu,
      Gly, Leu, Asn, Gln, Arg, Ser, Thr, Val, Lys, or
      Asp
<220> FEATURE:
<221> NAME/KEY: SITE
<222> LOCATION: (11)
<223> OTHER INFORMATION: This site is not invariant across RecA homologs
      and has been observed to contain Ala, Ile, Leu, or
      Val
<220> FEATURE:
<221> NAME/KEY: SITE
<222> LOCATION: (12)
<223> OTHER INFORMATION: This site is not invariant across RecA homologs
      and has been observed to contain Leu, Met, or Thr
<220> FEATURE:
<221> NAME/KEY: SITE
<222> LOCATION: (13)
<223> OTHER INFORMATION: This site is not invariant across RecA homologs
      and has been observed to contain Gly, Gln, Ala,
      Asn, or Ser
<220> FEATURE:
<221> NAME/KEY: SITE
<222> LOCATION: (14)
<223> OTHER INFORMATION: This site is not invariant across RecA homologs
```

```
            and has been observed to contain Ala, Ile, Ser,
            Thr, Val, Gly, or Leu, and this site is not
            present in some homologs
<220> FEATURE:
<221> NAME/KEY: SITE
<222> LOCATION: (17)
<223> OTHER INFORMATION: This site is not invariant across RecA homologs
            and has been observed to contain Leu, Phe, Ile,
            Val, Tyr, or Met
<220> FEATURE:
<221> NAME/KEY: SITE
<222> LOCATION: (18)
<223> OTHER INFORMATION: This site is not invariant across RecA homologs
            and has been observed to contain Pro, Glu, Met,
            Phe, Gln, Arg, or Val
<220> FEATURE:
<221> NAME/KEY: SITE
<222> LOCATION: (19)
<223> OTHER INFORMATION: This site is not invariant across RecA homologs
            and has been observed to contain Met, Gly, Lys,
            Arg, Thr, Ala, Pro, or Ser
<220> FEATURE:
<221> NAME/KEY: SITE
<222> LOCATION: (20)
<223> OTHER INFORMATION: This site is not invariant across RecA homologs
            and has been observed to contain Gly, Leu, Met,
            Ala, His, Gln, or Arg
<220> FEATURE:
<221> NAME/KEY: SITE
<222> LOCATION: (21)
<223> OTHER INFORMATION: This site is not invariant across RecA homologs
            and has been observed to contain Arg, Gln, Ser,
            Gly, Thr, or Val
<220> FEATURE:
<221> NAME/KEY: SITE
<222> LOCATION: (22)
<223> OTHER INFORMATION: This site is not invariant across RecA homologs
            and has been observed to contain Ile, Val, Ala,
            Leu, or Met
<220> FEATURE:
<221> NAME/KEY: SITE
<222> LOCATION: (23)
<223> OTHER INFORMATION: This site is not invariant across RecA homologs
            and has been observed to contain Val, Ile, Thr, or
            Tyr
<220> FEATURE:
<221> NAME/KEY: SITE
<222> LOCATION: (25)
<223> OTHER INFORMATION: This site is not invariant across RecA homologs
            and has been observed to contain Ile, Val, Ala,
            Leu, Met, or Phe
<220> FEATURE:
<221> NAME/KEY: SITE
<222> LOCATION: (26)
<223> OTHER INFORMATION: This site is not invariant across RecA homologs
            and has been observed to contain Tyr, Phe, Ala,
            Gly, or Val

<400> SEQUENCE: 2

Xaa Xaa Xaa Xaa Xaa Xaa Xaa Xaa Xaa Xaa Xaa Xaa Xaa Xaa Gly Gly
  1               5                  10                  15

Xaa Xaa Xaa Xaa Xaa Xaa Xaa Glu Xaa Xaa
              20                  25

<210> SEQ ID NO 3
<211> LENGTH: 26
<212> TYPE: PRT
<213> ORGANISM: Escherichia coli
<220> FEATURE:
<221> NAME/KEY: NON_TER
<222> LOCATION: (1)
<220> FEATURE:
<221> NAME/KEY: NON_TER
<222> LOCATION: (26)
<220> FEATURE:
<221> NAME/KEY: HELIX
```

-continued

```
<222> LOCATION: (6)..(12)
<223> OTHER INFORMATION: Alpha-helix B
<220> FEATURE:
<221> NAME/KEY: STRAND
<222> LOCATION: (22)..(26)
<223> OTHER INFORMATION: Beta-strand 1
<220> FEATURE:
<221> NAME/KEY: SIMILAR
<222> LOCATION: (1)..(26)
<223> OTHER INFORMATION: Non "Xaa" residues are the invariant and
      semiconservative elements of the MAW motif in RecA
      and its homologs
<220> FEATURE:
<221> NAME/KEY: SITE
<222> LOCATION: (2)
<223> OTHER INFORMATION: This site is neither invariant nor
      semiconservative across RecA homologs and has been
      observed to contain Ser, Gly, Lys, Pro, Thr, or
      Arg
<220> FEATURE:
<221> NAME/KEY: SITE
<222> LOCATION: (5)
<223> OTHER INFORMATION: This site is neither invariant nor
      semiconservative across RecA homologs and has been
      observed to contain Ser, Ala, Cys, Ile, Asn, Asp,
      or Phe
<220> FEATURE:
<221> NAME/KEY: SITE
<222> LOCATION: (6)
<223> OTHER INFORMATION: This site is neither invariant nor
      semiconservative across RecA homologs and has been
      observed to contain Leu, Ile, Thr, Val, Tyr, Lys,
      Gln, Asp, Pro, or Arg
<220> FEATURE:
<221> NAME/KEY: SITE
<222> LOCATION: (7)
<223> OTHER INFORMATION: This site is neither invariant nor
      semiconservative across RecA homologs and has been
      observed to contain Ser, Ala, Asp, Gly, Leu, Met,
      Thr, Val, Tyr, Glu, Asn, or Gln
<220> FEATURE:
<221> NAME/KEY: SITE
<222> LOCATION: (10)
<223> OTHER INFORMATION: This site is neither invariant nor
      semiconservative across RecA homologs and has been
      observed to contain Ile, Ala, Glu, Gly, Leu, Asn,
      Gln, Arg, Ser, Thr, Val, Lys, or Asp
<220> FEATURE:
<221> NAME/KEY: SITE
<222> LOCATION: (13)
<223> OTHER INFORMATION: This site is neither invariant nor
      semiconservative across RecA homologs and has been
      observed to contain Gly, Gln, Ala, Asn, or Ser
<220> FEATURE:
<221> NAME/KEY: SITE
<222> LOCATION: (14)
<223> OTHER INFORMATION: This site is neither invariant nor
      semiconservative across RecA homologs and has been
      observed to contain Ala, Ile, Ser, Thr, Val, Gly,
      or Leu, and this site is not present in some
      homologs
<220> FEATURE:
<221> NAME/KEY: SITE
<222> LOCATION: (18)
<223> OTHER INFORMATION: This site is neither invariant nor
      semiconservative across RecA homologs and has been
      observed to contain Pro, Glu, Met, Phe, Gln, Arg,
      or Val
<220> FEATURE:
<221> NAME/KEY: SITE
<222> LOCATION: (19)
<223> OTHER INFORMATION: This site is neither invariant nor
      semiconservative across RecA homologs and has been
      observed to contain Met, Gly, Lys, Arg, Thr, Ala,
      Pro, or Ser
<220> FEATURE:
<221> NAME/KEY: SITE
<222> LOCATION: (21)
<223> OTHER INFORMATION: This site is neither invariant nor
```

```
                            -continued semiconservative across RecA homologs and has been
    observed to contain Arg, Gln, Ser, Gly, Thr, or
    Val

<400> SEQUENCE: 3

Ile Xaa Thr Gly Xaa Xaa Xaa Leu Asp Xaa Ala Leu Xaa Xaa Gly Gly
 1               5                  10                  15

Leu Xaa Xaa Gly Xaa Ile Val Glu Ile Tyr
            20                  25
```